United States Patent [19]

Walton

[11] 4,284,947
[45] Aug. 18, 1981

[54] DETECTING THE SIZE AND SHAPE OF BODIES

[75] Inventor: Hyman Walton, Beckermet, England

[73] Assignee: United Kingdom Atomic Energy Authority, London, England

[21] Appl. No.: 56,324

[22] Filed: Jul. 10, 1979

[30] Foreign Application Priority Data

Aug. 8, 1978 [GB] United Kingdom ............... 32600/78

[51] Int. Cl.³ ............................................. G01R 27/26
[52] U.S. Cl. .................................. 324/61 R; 209/517; 209/572
[58] Field of Search ............. 324/61 R; 209/517, 571, 209/572; 73/104

[56] References Cited

U.S. PATENT DOCUMENTS

| 2,666,896 | 1/1954 | Harris | 324/61 R |
|---|---|---|---|
| 3,188,564 | 6/1965 | Felix | 324/61 R |
| 3,207,979 | 9/1965 | Perkins | 324/61 R |
| 3,209,247 | 9/1965 | Mead et al. | 324/61 R |
| 3,215,931 | 11/1965 | Schooley, Jr. | 324/61 R |
| 3,519,922 | 7/1970 | Nash et al. | 324/61 R |
| 3,723,865 | 3/1973 | Batey et al. | 324/61 R |
| 3,993,194 | 11/1976 | Reuland | 209/571 X |
| 4,086,528 | 4/1978 | Walton | 324/61 R |
| 4,208,625 | 6/1980 | Piso | 324/61 R |

FOREIGN PATENT DOCUMENTS 574600 9/1977 U.S.S.R. ............................... 324/61 R

Primary Examiner—Stanley T. Krawczewicz
Attorney, Agent, or Firm—Larson, Taylor and Hinds

[57] ABSTRACT

The size and shape of a body is determined by rolling it between the plates of capacitors, the dielectric constant of which is thereby changed. A capacitor scans sections of the body along its longitudinal axis to detect its diameter and surface faults, a second determines the body's length and a third determines the position of the body. The changes in dielectric constant are compared with those produced by a body of known size and shape so that the size and shape of the body can be determined.

14 Claims, 3 Drawing Figures

DETECTING THE SIZE AND SHAPE OF BODIES

BACKGROUND OF THE INVENTION

The invention relates to determination of the size and shape of bodies, particularly though not exclusively, pellets for insertion into nuclear fuel pins. The pellets are of right cylindrical shape and their geometry has to be accurately known and controlled.

SUMMARY OF THE INVENTION

The pellets are rolled down a slope. Two wires arranged parallel to and respectively above and below the slope are disposed diagonally across the slope. The wires are connected as a capacitor and as a pellet rolls down the slope, sections of the pellet between the capacitor wires are scanned. The dielectric constant of the capacitor changes in response to changes in the amount of pellet between the wires.

A second capacitor is arranged underneath the slope and this capacitor has converging wires on plates so that as the pellet rolls down the slope there is progressively less of the pellet between wires. Consequently the dielectric constant of the capacitor changes as the pellet rolls down the slope so that the position of the pellet can be determined.

A third capacitor has a probe each side of the slope, respectively, so that the length of the pellet can be determined. The changes in dielectric constant of the capacitors are analysed by processing circuitry via charge capacitors.

DESCRIPTION OF THE DRAWINGS

An embodiment of the present invention will now be described by way of example only with reference to the accompanying drawings in which.

DESCRIPTION OF THE PREFERRED EMBODIMENT

The invention is conveniently used for detecting the size and shape of right cylindrical pellets intended for insertion in nuclear fuel pins. Such pellets may, for example, comprise polymethylmethacrylate resin sold under the Registered Trade Mark "PERSPEX" or brass and uranium oxide.

Figure 1:
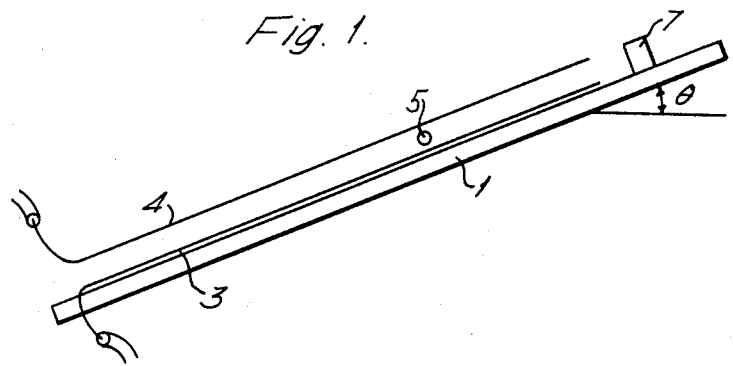
FIG. 1 is a diagrammatic side view of apparatus for performing a method of detecting the size and shape of a body.
Figure 2:
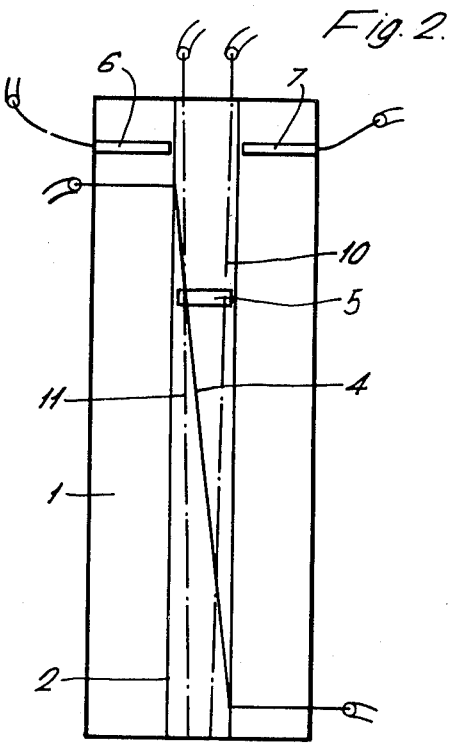
FIG. 2 is a plan view of the apparatus shown in FIG. 1.

In FIGS. 1 and 2 there is shown a slope 1 having channel 2 which forms a fixed path down which the pellets to be examined roll. The slope is inclined at an angle $\theta$ to the horizontal and the value of $\theta$ is chosen so that pellets roll down the slope at a satisfactory rate without bouncing from the surface of the base of the channel. A convenient value for $\theta$ is about 10°.

The base of the channel 2 supports an oscillator wire 3 to which an alternating carrier signal is applied. A detector wire 4 is supported above the channel and runs parallel to the oscillator wire 3. The wires 3 and 4 form the plates of a capacitor. A pellet 5 rolling down the channel passes between the wires 3, 4 which are inclined across the channel 2. Therefore, the electric field of the capacitor comprising the wires 3, 4 intersects the fixed path at different points along the breadth thereof along the length of said fixed path. The length of the channel 2 is such that the pellet undergoes several revolutions whilst between the wires 3, 4. As the pellet rolls down the slope the cylindrical surface is progressively exposed to the wires 3, 4 and the surface is scanned by the capacitor. A convenient channel length is about fifteen times the pellet circumference. The rolling pellet causes changes in the dielectric constant of the capacitor system and the change is monitored by apparatus such as that described with reference to FIG. 3 below and FIG. 3 of British Patent Specification No. 1,517,364. The capacitor formed by the wires 3, 4 would be connected to the point B in the last mentioned Figure and a suitably-sized reference capacitor would be connected to the point C.

The capacitor formed by the wires 3, 4 may be used to detect defects in the surface of the pellet along its longitudinal axis, differences in diameter and differences in the shape of the pellets. From the nature of the changes in capacitance it may be possible to detect if the pellet is non-circular in cross-section or if its cross-section varies along the length of the pellet as would occur if the pellet were tapered or in the shape of a barrel (increased diameter at the centre) or diabolo (increased diameter at the ends). Additional means to be described hereinafter are required to detect variations in the length of the pellets, and in pellets of annular cross-section to detect faults such as total or partial blocking of the central aperture or non-central location of the aperture. In FIGS. 1 and 2 there are shown two capacitance probes 6, 7 located on opposite sides of the channel in the slope at a higher level than the wires 2, 3. As a pellet passes between the probes one of which, is supplied with an alternating carrier signal, the dielectric constant of the capacitor system formed by the two probes 6, 7 changes. By comparison of the changes with those obtained when a standard pellet of known length and configuration passes between the probes it is possible to detect pellets which differ from the standard and reject those which fall outside the chosen tolerance limits. The carrier signal applied to the one of said probes may be the same as that applied to the wires 2, 3.

Alternatively it may be desirable to utilise a different carrier signal for the probes such as one with a higher peak to peak oscillating voltage. In the former case the capacitor systems formed by the wires 2, 3 and the probes 6, 7 may be connected in series to point B of the apparatus illustrated in FIG. 3 of British Patent Specification No. 1,517,364. In the latter case the capacitor systems formed by the wires 2, 3 and the probes are coupled to two of the arms of a four terminal network having four arms (that is one of them is coupled to B and the other to C of the above-mentioned FIG. 3). This arrangement is illustrated in FIG. 3 of the present application and will be described below.

If the pellets were all sufficiently similar that the time they took to roll down the slope was substantially the same for each one then the comparison of their shape along their longitudinal axis could be made on the basis of the output signal at a particular time interval. However for pellets which show a divergence of rolling times the comparison is better made on the basis of the output signal when the pellet is at a particular point on the plane 1. A position detecting system is incorporated into the plane 1 as can be seen from FIG. 2 in which two wires 10, 11 (shown chain dotted) are located at the bottom of the channel 2. The distance between the wires 10, 11 decreases towards the bottom of the inclined plane 1 and so as the pellet rolls down the channel 2 the dielectric constant between the wires changes progressively. A carrier frequency different from that applied to the capacitor systems formed by the wires 2, 3 and probes 6, 7 must be used for the position-detecting capacitor system comprising the wires 10, 11 to eliminate cross-coupling effects. The output from the position-detecting capacitor system is passed to an independent amplifier. The use of position rather than time as a basis for the comparison of the output signal from a standard pellet and a pellet under examination eliminates differences caused by different rolling times.

Figure 3:
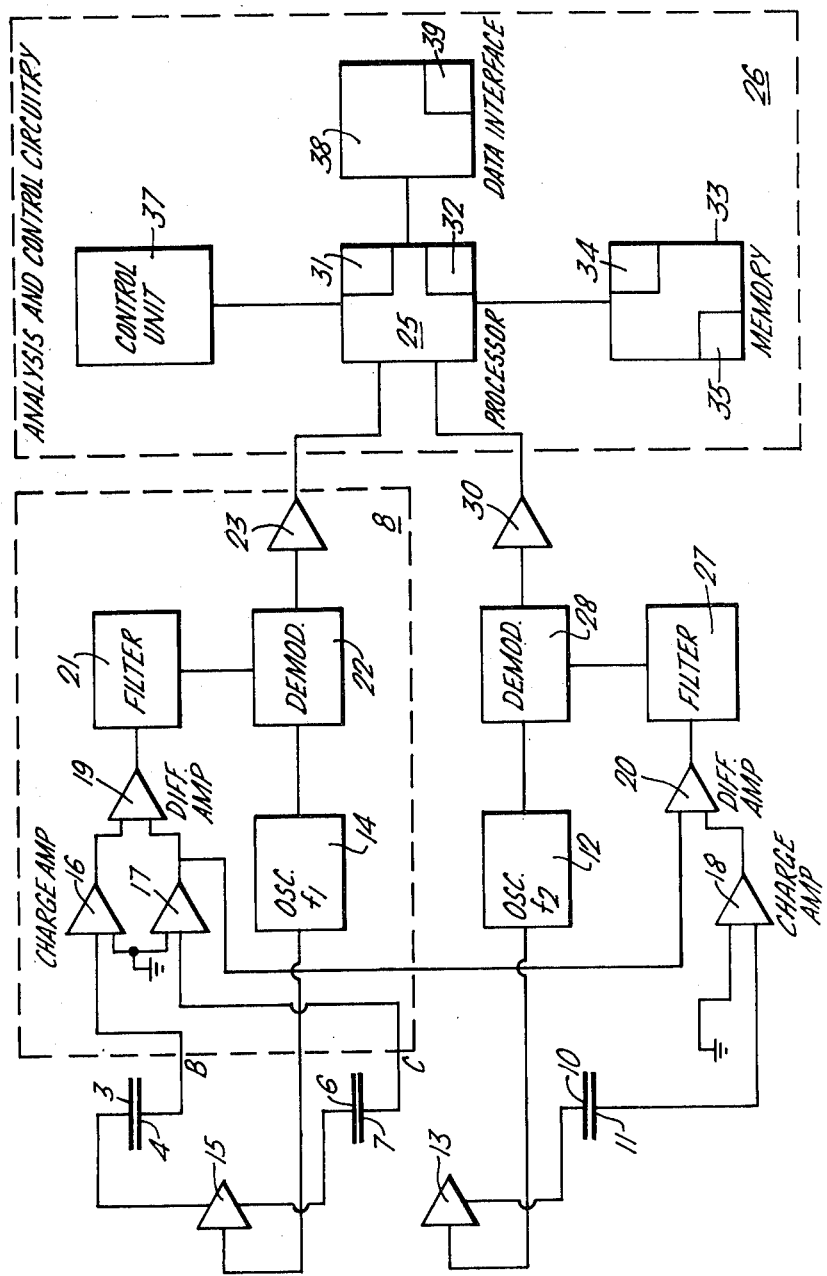
FIG. 3 is an incomplete electrical circuit diagram partly in block form for detecting and processing changes in electrical parameters occuring in the apparatus of FIGS. 1 and 2.

Reference is now made to FIG. 3, wherein like reference numerals are used for like parts as in FIGS. 1 and 2. A buffered driver signal at frequency $f_1$ for the capacitors 3, 4; 6, 7 is provided at differing magnitude for each capacitor, from an oscillator arrangement 14 through a buffering amplifier arrangement 15. The capacitor 10, 11 receives a separate buffered driver signal at frequency $f_2$ from oscillator arrangement 12 via buffering amplifier 13 to avoid interference between the detector systems. The wire 4 is connected to a charge amplifier 16, the capacitance probe 7 to a charge amplifier 17 and the wire 11 to a charge amplifier 18. A charge amplifier is a DC operational amplifier with a capacitive feedback which can produce a voltage output directly proportional to the change in charge at its input terminals. The output of charge amplifiers 16 and 17 are fed to a differential amplifier 19. The output from amplifier 17 is also tapped for feeding to a differential amplifier 20 as will be described below. The differential amplifier 19 has its output connected to a bandpass filter 21 and then via a demodulator 22 and an amplifier 23 to a signal processing unit 25 in analysis and control circuitry 26.

The charge amplifier 18 has its output connected to the differential amplifier 20, the other input to the amplifier 20 being from charge amplifier 17 as mentioned above. The output of the differential amplifier 20 is to the signal processing unit via similar circuitry to that used in relation to the amplifier 19, in the case of amplifier 20 being via band pass filter 27, demodulator 28 and amplifier 30.

The signal processing unit 25 comprises comparators 31 and 32 for comparing values of input signals with stored values in a memory unit 33. The memory unit 33 includes remembered and desired values of signals from the differential amplifiers 19 and 20 in units 34 and 35, respectively, operating in conjunction with comparators 31 and 32, respectively. The memory unit 33 can be programmed with desired preselected values of signals or it can be programmed by running a reference pellet of desired size and shape characteristics down the slope 1. The unit 25 can control a unit 37 provided for rejecting pellets of unsuitable shape, for example by effecting opening or closure of electrohydraulic gates at the bottom of slope 1.

The unit 25 is connected to a data interface 38 so that data can be transmitted to a central control or other processor, if necessary, and the interface 38 is provided with a display 39 for example an oscilloscope or visual display unit so that the shape of pellets can be seen visually.

In operation of the circuitry of FIG. 3, suppose that a pellet of unknown size and shape which may or may not be satisfactory is put at the top of the slope ready for rolling. The memory unit 33 will already have been programmed with desired values of shape and a range of allowed values manually and also by rolling a reference pellet down the slope 1. The unknown pellet is first checked for size in order that its length is not so great as to render it unsatisfactory for nuclear use. This first checking is effected by the capacitance probes 6 and 7, since as the pellet rolls between the probes, the dielectric constant of the capacitor comprising probes 6 and 7 changes, thereby causing the voltage from charge amplifier 17 to change which in turn causes a change in value of the output of amplifier 19 which varies the input into unit 26. The memory unit 33 contains a range of desired values of the signal in the unit 34 and if the memory signal from the amplifier 23 falls outside this range as determined by comparator 31, then the pellet is rejected. A reference value of capacitance for the differential amplifier is provided by the charge amplifier 16 which has a constant output because the capacitor 3, 4 is not yet in use.

Assuming that the pellet has not been rejected then it will continue to roll down the slope 1 and will roll between the wires 3, 4. The part of the pellet, for the time being between the wires 3, 4 will determine the capacitance of the capacitor 3, 4. Reference to FIG. 2 will show that a different section of the pellet is between the wires 3, 4 depending on where the pellet is down the slope 1. Thus the measured value of capacitance is dependant upon the section of the pellet for the time being between the wires 3 and 4. Consequently, the size and shape of the pellet at that section is determined because the voltage output of amplifier 19 changes and then the signal to circuitry 26 via filter 21, demodulator 22 and amplifier 23 changes. The memory 34 contains known values of capacitance for known sizes and shapes and these are compared with the incoming signal in the comparator 31.

In order that the size and shape of the whole pellet can be determined, it is necessary that information be provided as to how far down the slope the pellet has rolled. This information is provided by the capacitor constituted by the wires 10, 11 since as the pellet rolls down the slope, the capacitance of this capacitor (redielectric constant) changes because progressively less of the pellet comes between the wires owing to their relative approach. Thus the capacitance of capacitor 10, 11 is a measure of how far down the slope the pellet has rolled. The change in capacitance causes a change in output of the amplifier 18 and also that of amplifier 20, thereby to feed a changed input signal into circuitry 26 from amplifier 30.

The capacitor 3, 4 is used initially as the reference capacitor for capacitor 6, 7 and thereafter the capacitor 6, 7 as reference capacitor for the capacitors 3, 4 and 10, 11. This is possible because the value of capacitance of the capacitor 6, 7 varies initially and is then constant, whereas the value of capacitance of the capacitor 3, 4 is constant initially and then varies, there being only one pellet in the system at a time. This is due to the geometry of the slope layout as can best be seen in FIG. 2. A reference capacitor is used in this function when constant. Owing to the function of differential amplifier 19, the signal to the processing circuitry 26 will be of different polarity, dependent upon which of the capacitors 3, 4 or 6, 7 is being altered by the pellet. This difference in polarity enables the circuitry to deduce which of the capacitors is in operation. A similar situation obtains mutatis mutandis in the case of the capacitors 6, 7 and 10, 11.

The data as to size and shape of the pellets derived in the unit 25 can be transmitted to other data processing units by means of the data transmission interface 38. The size and shape of the pellets can be displayed on the display 39 for the convenience of operators.

In some embodiments of the invention, the nature of the material being scanned by the capacitors is determined.

I claim:

1. A method of detecting information as to the shape and size of a body comprising moving the body along a fixed path, arranging the plates of a capacitor so that the electric field of the capacitor cuts the path at different points across the breadth of the path along the length of said path, detecting changes in dielectric constant of the capacitor caused by movement of said body along said fixed path, comparing the changes so detected with changes caused by a reference body of known size and shape and deducing from the comparison information as to the size and shape of the body.

2. A method as claimed in claim 1, in which the position of the body along the path in relation to the plates is determined by measuring changes in dielectric constant of a second capacitor, said changes being caused by changes in the position, the plates of the second capacitor having different relative dispositions along said path.

3. A method as claimed in claim 1, in which movement between the plates by the body is effected by rolling thereof.

4. Apparatus for detecting information as to the shape and size of a body, comprising a capacitor, between the plates of which the body is moveable along a fixed path, the electric field of the capacitor plates cutting the path at different points across the breadth of the path along the length of said path, circuit means for determining changes in dielectric constant of the capacitor caused by said movement of the body along the path between the plates, and comparator means for comparing said changes with changes in dielectric constant constant caused by a reference body of known size and shape thereby to determine information as to the size and shape of a body.

5. Apparatus as claimed in claim 4, in which the capacitor comprises parallel wires.

6. Apparatus as claimed in claim 5, in which said fixed path comprises a slope whereon the body is moved by rolling thereof.

7. Apparatus as claimed in claim 6, in which the parallel wires are disposed obliquely across the slope.

8. Apparatus as claimed in claim 7, in which the wires are longer than the maximum rolling circumference of the body.

9. Apparatus as claimed in claim 4, further comprising means for determining the position of the body along the path between the plates of the capacitor, said last mentioned means comprising a second capacitor having plates which have different relative dispositions along the length of said slope.

10. Apparatus as claimed in claim 9, in which the second capacitor has plates comprising wires and the wires are convergent.

11. Apparatus as claimed in claim 4, further comprising means for determining if the maximum length of the body exceeds a preselected level.

12. Apparatus as claimed in claim 11, in which the last mentioned means comprises a third capacitor.

13. Apparatus for use in extracting information concerning a body, comprising means defining a fixed path along which the body moves translationally while rotating about an axis normal to the direction of translation, a capacitor having its plates arranged such that the body moves between the plates as it traverses said path, said plates being elongate and parallel and disposed obliquely to said fixed path such that the electric field of the plates cuts obliquely across said fixed path and intersects the moving body at different points along its said axis as the body traverses said path, and means for detecting changes in dielectric constant of the capacitor caused by movement of the body along said path.

14. Apparatus as claimed in claim 13 wherein said fixed path comprises an inclined surface along which said body rolls, and said capacitor plates comprise parallel wires.

* * * * *